(12) United States Patent
Granato et al.

(10) Patent No.: US 11,791,034 B2
(45) Date of Patent: Oct. 17, 2023

(54) ADAPTIVE ARTIFICIAL INTELLIGENCE SYSTEM FOR IDENTIFYING BEHAVIORS ASSOCIATED WITH MENTAL ILLNESS AND MODIFYING TREATMENT PLANS BASED ON EMERGENT RECOGNITION OF ABERRANT REACTIONS

(71) Applicant: Federal Leadership Institute, Inc., McLean, VA (US)

(72) Inventors: Laura Granato, McLean, VA (US); Michael M. Kohonoski, Leesburg, VA (US); Thomas Reigle, Woodbridge, VA (US)

(73) Assignee: Federal Leadership Institute, Inc., McLean, VA (US)

( * ) Notice: Subject to any disclaimer, the term of this patent is extended or adjusted under 35 U.S.C. 154(b) by 0 days.

(21) Appl. No.: 18/161,601

(22) Filed: Jan. 30, 2023

(65) Prior Publication Data

US 2023/0170076 A1 Jun. 1, 2023

Related U.S. Application Data

(63) Continuation of application No. 15/956,421, filed on Apr. 18, 2018, now Pat. No. 11,568,979.

(51) Int. Cl.
| | |
|---|---|
| G16H 20/70 | (2018.01) |
| G16H 50/50 | (2018.01) |
| G16H 10/60 | (2018.01) |
| G16H 50/70 | (2018.01) |
| G16H 50/20 | (2018.01) |
| G06N 20/00 | (2019.01) |

(52) U.S. Cl.
CPC ............. *G16H 20/70* (2018.01); *G06N 20/00* (2019.01); *G16H 10/60* (2018.01); *G16H 50/20* (2018.01); *G16H 50/50* (2018.01); *G16H 50/70* (2018.01)

(58) Field of Classification Search
CPC ........ G16H 20/70; G16H 10/60; G16H 50/20; G16H 50/50; G16H 50/70; G06N 20/00; A61B 5/163; A61B 5/7267; A61B 5/165; A61B 5/02055; A61B 5/021; A61B 5/024; A61B 5/0533; A61B 5/11; G06F 2218/12
See application file for complete search history.

(56) References Cited

U.S. PATENT DOCUMENTS

| | | | |
|---|---|---|---|
| 10,176,163 B2 * | 1/2019 | Clark | G06F 40/279 |
| 11,436,549 B1 * | 9/2022 | Hull | H04W 4/38 |
| 11,538,583 B2 * | 12/2022 | Isobe | G16H 10/60 |

(Continued)

FOREIGN PATENT DOCUMENTS

WO WO-2017106770 A1 * 6/2017 .......... A61B 5/0022

*Primary Examiner* — Ryan W Sherwin
(74) *Attorney, Agent, or Firm* — COOLEY LLP (57) ABSTRACT

One or more embodiments described herein relate to predicting, using adaptive artificial intelligence techniques, typical and aberrant physiological reactions of a patient to psychiatric counseling. Treatment plans can be determined and calculated based on previously-gathered demographic and/or biometric data, and/or modifications to treatment plans can be determined and/or implemented based on emergent recognition of reaction types, such as reclassifying reactions that would previously have been deemed typical as aberrant (or vice versa).

20 Claims, 10 Drawing Sheets

(56) References Cited

U.S. PATENT DOCUMENTS

| | | | |
|---|---|---|---|
| 2009/0016600 A1* | 1/2009 | Eaton | G06V 20/47 |
| | | | 382/103 |
| 2010/0010371 A1* | 1/2010 | Zayfert | G16H 20/70 |
| | | | 600/558 |
| 2015/0370993 A1* | 12/2015 | Moturu | G16H 50/50 |
| | | | 703/6 |
| 2015/0370994 A1* | 12/2015 | Madan | G16H 15/00 |
| | | | 705/3 |
| 2019/0147367 A1* | 5/2019 | Bellamy | G06N 5/022 |
| | | | 706/12 |
| 2019/0189259 A1* | 6/2019 | Clark | G16H 10/60 |

* cited by examiner

FIG. 1

Patient Database Record

| Unique Identifier | Element No. | Description | Weighting Factor | Sample Data |
|---|---|---|---|---|
| 1298456 | 1 | Age | 10 | 47 |
| 1298456 | 2 | Sex | 20 | Male |
| 1298456 | 3 | Marital Status | 70 | Divorced |
| 1298456 | 3 | Counseling Need | 100 | PTSD |
| 1298456 | 4 | Education Level | 50 | High School |
| 1298456 | 5 | Military Service | 80 | Yes |
| 1298456 | 6 | Rank | 65 | Major |
| 1298456 | 7 | Branch of Military | 95 | U.S. Army |
| 1298456 | 8 | Convicted of felony | 25 | No |
| 1298456 | 9 | Prior treatment duration | 35 | 720 days |
| 1298456 | 10 | Permission for biometric monitoring | 15 | Yes |
| 1298456 | 11 | Agree to Remote/Video treatment | 15 | Yes |
| 1298456 | 12 | Referring party | 20 | U.S. Government |
| 1298456 | 13 | Accepted for treatment | 10 | Yes |
| N | N | N | N | N |

FIG. 2

Patient Biometric Feedback Record

| Unique Identifier | Meeting Date | Time | Heart Rate | Blood Pressure | Skin Conductivity | Excessive Eye Movement | Excessive Head/Body Movement |
|---|---|---|---|---|---|---|---|
| 1298456 | 2/1/2017 | 13:01:00 | 60 | 120/80 | 05.456 | No | No |
| 1298456 | 2/1/2017 | 13:02:00 | 60 | 120/80 | 05.556 | No | No |
| 1298456 | 2/1/2017 | 13:03:00 | 65 | 130/75 | 05.666 | No | Yes |
| 1298456 | 2/1/2017 | 13:04:00 | 70 | 140/80 | 05.726 | No | Yes |
| 1298456 | 2/1/2017 | 13:05:00 | 90 | 160/90 | 05.806 | Yes | Yes |
| 1298456 | 2/1/2017 | 13:06:00 | 85 | 155/90 | 05.784 | Yes | Yes |
| 1298456 | 2/1/2017 | 13:07:00 | 90 | 150/80 | 06.456 | Yes | Yes |
| 1298456 | 2/1/2017 | 13:08:00 | 95 | 160/85 | 06.896 | Yes | Yes |
| 1298456 | 2/1/2017 | 13:09:00 | 75 | 135/80 | 06.456 | No | Yes |
| 1298456 | 2/1/2017 | 13:10:00 | 70 | 130/75 | 06.294 | No | No |
| 1298456 | 2/1/2017 | 13:11:00 | 65 | 125/75 | 05.873 | No | No |
| 1298456 | 2/1/2017 | 13:12:00 | 60 | 120/80 | 05.686 | No | No |
| 1298456 | 2/1/2017 | 13:13:00 | 60 | 120/80 | 05.456 | No | No |

FIG. 3

Counselor Database Record

| Unique Identifier | Element No. | Description | Weighting Factor | Sample Data |
|---|---|---|---|---|
| 5742981 | 1 | Age | 30 | 47 |
| 5742981 | 2 | Sex | 20 | Male |
| 5742981 | 3 | Years of Experience | 90 | 23 |
| 5742981 | 4 | Education Level | 25 | PhD |
| 5742981 | 5 | Marital Status | 80 | Single |
| 5742981 | 6 | School | 25 | Johns Hopkins |
| 5742981 | 7 | Case 1 Counseling Need | 80 | PTSD |
| 5742981 | 8 | Case 1 time to complete treatment | 75 | 320 days |
| 5742981 | 9 | Case 1 outcome | 100 | Positive |
| 5742981 | 10 | Case 1 number of patient complaints | 90 | 2 |
| 5742981 | 11 | Case 1 Biometric Behavior | 85 | Aberrant |
| 5742981 | 12 | Case 2 Counseling Need | 80 | Marriage |
| 5742981 | 13 | Case 2 time to complete treatment | 90 | 186 days |
| 5742981 | 14 | Case 2 outcome | 100 | Negative |
| 5742981 | 15 | Case 2 number of patient complaints | 90 | 6 |
| 5742981 | 16 | Case 2 Biometric Behavior | 85 | Normal |
| N | N | N | N | N |

FIG. 4

Mental Illness Counseling Treatment Plan Database

| Unique Identifier | Counseling Need | Sample Data |
|---|---|---|
| 6349180 | PTSD | In-person, no remote video, twice a week, 16 week duration, with biometrics |
| 6349181 | PTSD | In-person, remote video, once a week, 12 week duration, no biometrics |
| 6349182 | PTSD | No in person, remote video only, twice per month, 20 week duration, no biometrics |
| 6349183 | Divorce | In-person, remote video, with spouse, every two weeks, 24 week duration, with biometrics |
| 6349184 | Divorce | In-person, remote video, no spouse, every two weeks, 24 week duration, no biometrics |
| 6349186 | Depression | In-person, remote video, daily, 52 week duration, with biometrics |
| 6349187 | Depression | No in-person, remote video, once per week, 52 week duration, no biometrics |
| 6349189 | Substance | No in-person, no video, telephone only, daily, 16 week duration, no biometrics |
| 6349191 | Anger | In-person, no remote video, twice a week, 16 week duration, with biometrics |
| 6349192 | Anger | In-person, remote video, once a week, 12 week duration, no biometrics |
| N | N | N |

FIG. 5

Counseling Event Record Database

| Patient Unique Identifier | Counselor Unique Identifier | Treatment Plan Unique Identifier | Total Meetings this Patient | Total Meetings this Plan | Meeting Date | Meeting Time | Counselor Assessment | Patient Assessment | Biometric Behavior | Treatment Review or Change Required |
|---|---|---|---|---|---|---|---|---|---|---|
| 1298456 | 5742981 | 6349180 | 47 | 47 | 11/1/2017 | 1300 | Positive | Positive | Normal | No |
| 1298456 | 5742981 | 6349180 | 48 | 48 | 11/13/2017 | 1400 | Negative | Negative | Aberrant | Yes |
| 1298456 | 5742981 | 6349182 | 49 | 1 | 11/20/2017 | 1300 | Positive | Positive | Aberrant | No |
| 1298998 | 5742099 | 6349186 | 1 | 1 | 9/8/2017 | 0900 | Positive | Positive | Normal | No |
| 1298998 | 5742099 | 6349186 | 2 | 2 | 9/15/2017 | 0900 | Positive | Positive | Normal | No |
| 1298422 | 5742100 | 6349192 | 1 | 1 | 10/1/2017 | 0800 | Negative | Negative | Aberrant | Yes |
| 1298422 | 5742075 | 6349192 | 2 | 2 | 10/5/2017 | 0800 | Positive | Positive | Normal | No |

ADAPTIVE ARTIFICIAL INTELLIGENCE SYSTEM FOR IDENTIFYING BEHAVIORS ASSOCIATED WITH MENTAL ILLNESS AND MODIFYING TREATMENT PLANS BASED ON EMERGENT RECOGNITION OF ABERRANT REACTIONS

CROSS-REFERENCE TO RELATED APPLICATIONS

This application is a continuation of U.S. patent application Ser. No. 15/956,421, filed Apr. 18, 2018, and titled "Adaptive Artificial Intelligence System for Identifying Behaviors Associated with Mental Illness and Modifying Treatment Plans Based on Emergent Recognition of Aberrant Reactions," the entire contents of which are hereby incorporated by reference.

TECHNICAL FIELD

One or more embodiments described herein relate to predicting, using adaptive artificial intelligence techniques, typical and aberrant physiological reactions of a patient to psychiatric counseling. Treatment plans can be determined and calculated based on previously gathered demographic and/or biometric data, and/or modifications to treatment plans can be determined and/or implemented based on emergent recognition of reaction types, such as reclassifying reactions that would previously have been deemed typical as aberrant (or vice versa).

BACKGROUND

It is estimated that 20% of the population of the United States (roughly 60 million people) experience a mental health disorder in any given year. Of these totals, only 45% are treated. This is especially concerning when 70% to 90% of those that are treated see an improvement in their symptoms and quality of life.

Most treatment options involve multiple sessions with an individual that is specially trained for treating the disorder. Treatment times vary from a few weeks to on-going therapy of indefinite duration.

The efficacy of the treatment plans depends on a number of factors, such as characteristics of the patient and his or her history and/or psyche, the illness, the counselor, the selection of treatment plan, and the administration of the treatment plan. A shortfall in this process is that any given counselor does not have the ability to know, on a large scale, in near real-time, the efficacy of other treatment plans administered by other counselors to individuals that have the same mental disorder.

That said, even the best treatment plans have a chance of not working for particular individuals suffering from a mental disorder. An additional challenge is to recognize when a treatment plan is not performing as intended or desired, to identify aberrant behavior and possible events that could cause serious harm to the patient and others, and to intervene to limit this where possible.

A need exists to regularly provide recommendations for treatment plan(s) or changes to that treatment plan(s) for patients with mental illness that includes a broad analysis of information concerning various treatment efficacies, the patient themselves, their biometrics, the illness type, and the abilities of the counselors that are available to administer the treatment. This will lower the overall cost and duration of treatment through optimization and therefore allow for greater percentages of the population that have a mental illness to be treated due to lower insurance reimbursement costs.

DETAILED DESCRIPTION

The present disclosure relates to an overall system and method for identifying patient behavior during a counseling session as typical or aberrant. Embodiments described herein are generally described in the context of treatments for patients with various types of mental illness. Embodiments described herein can be applied both the beginning of a treatment plan and for adjusting a treatment plan during its delivery, as well as identifying aberrant biometric behavior of the patient during the treatment process. Demographic, biometric, and time-based information can be collected and processed using a machine learning task, analytics, and/or "big data," to predict the best next steps for a patient with a mental illness that is under treatment by a professional counselor.

Biometric data that is to be incorporated in a predictive model of patient behavior can be collected, for example, using video streams, voice streams, wearable devices, handheld devices, smart phones, and other devices/techniques. Biometric data can be captured locally (e.g., via local wired or wireless connections) or transmitted to remote storage and/or compute device via an Internet connection. Biometric and other data described herein can stored either on a local server (collocated and/or remote from a patient and/or counselor) or be stored in the cloud (remote servers hosted on the Internet). Similarly, machine learning tasks described in further detail herein can be performed on a local server (collocated and/or remote from a patient) or in the cloud.

The demographic information collected for a number of patients can be processed in part and/or in total using a machine learning task to define or create a model of patient behavior (also referred to herein as a predictive model or simply a model). The model can be applied to demographic information for a specific (e.g., new) patient. If the demographic information for the specific patient matches a common pattern seen from other patients (e.g., of a similar demographic cohort to a new patient), then a new patient's starting treatment plan can be chosen or, if already in treatment, the treatment plan can be modified.

A machine learning task can process biometric and/or demographic data associated with patients who have undergone counseling sessions to produce a model for a patient. The model can be produced using data from all patients, from a specific patient, and/or from a cohort of demographically (or biometrically) similar patients. As described in further detail herein, biometric data from a target patient—a patient undergoing counseling—can be collected, stored and/or compared to other patients' biometric data (e.g., biometric data for remaining patients for whom biometric data is available, biometric data for that specific patient collected during a previous counseling session, and/or biometric data collected from an appropriate demographic cohort). If the target patient's biometric data is similar to a typical pattern seen from other patients, then the model can indicate that the target patient is having a typical reaction to the counseling session. If, however, the target patient's biometric data is dissimilar from typical patterns seen from other patients, or is similar to an aberrant pattern seen from other patients, then the model can indicate that the target patient is having an aberrant reaction to the counseling session. If an aberrant reaction is detected, a treatment plan for the target patient can be modified based, for example, upon the amount of time that the new patient has been in treatment.

The types of biometric data collected can include but are not limited to heart rate, blood pressure, skin conductivity, temperature, and movement. Biometric data can further include data obtained by analyzing captured video to determine eye movement, body perspective or language, facial expressions, etc. Additionally, biometric data can include data obtained by analyzing captured audio to determine word selection, sentence structure, pauses in response, length of response, and timeliness of response, etc. Patient demographic data could include but not be limited to age, sex, ethnicity, marital status, geography, income, and previous treatment history. Counselor demographic data could include but not be limited to age, sex, ethnicity, marital status, specialty, and previous history of successfully treating patients. Timing data could include but not be limited to the measurement of the length of time that a feedback session entails, or the amount of time it took a patient to schedule and provide feedback, or the time of the request by a patient for a non-planned treatment session, and timeliness of providing payment for services.

In some embodiments, demographic and prior treatment data for both patient and counselor are captured and/or stored before the beginning of any new treatment plan. Additional data can be collected during regular, predetermined, and/or ad hoc feedback intervals. Further data could be collected in face-to-face sessions with counselors or using other electronic devices of recording the audio and video treatment feedback or using real-time transmission for either streaming live to local or cloud servers. Counselors would also have the ability, for those sessions in which they were present, to provide input to the model on what they perceive from the patient feedback sessions. In the event that an internet connection is not readily available during the feedback session, a local compute device (e.g., collocated with the patient and/or counselor) can store the information temporarily; such data can be forwarded to an (optionally remote or cloud-based) compute device that can perform machine learning tasks, as described in further detail herein. All of the data collected for a particular patient can be associated with a unique identifier similar but not limited to a userid/password and can be implemented in such a way as to meet all government regulations on privacy and compliance.

Figure 1:
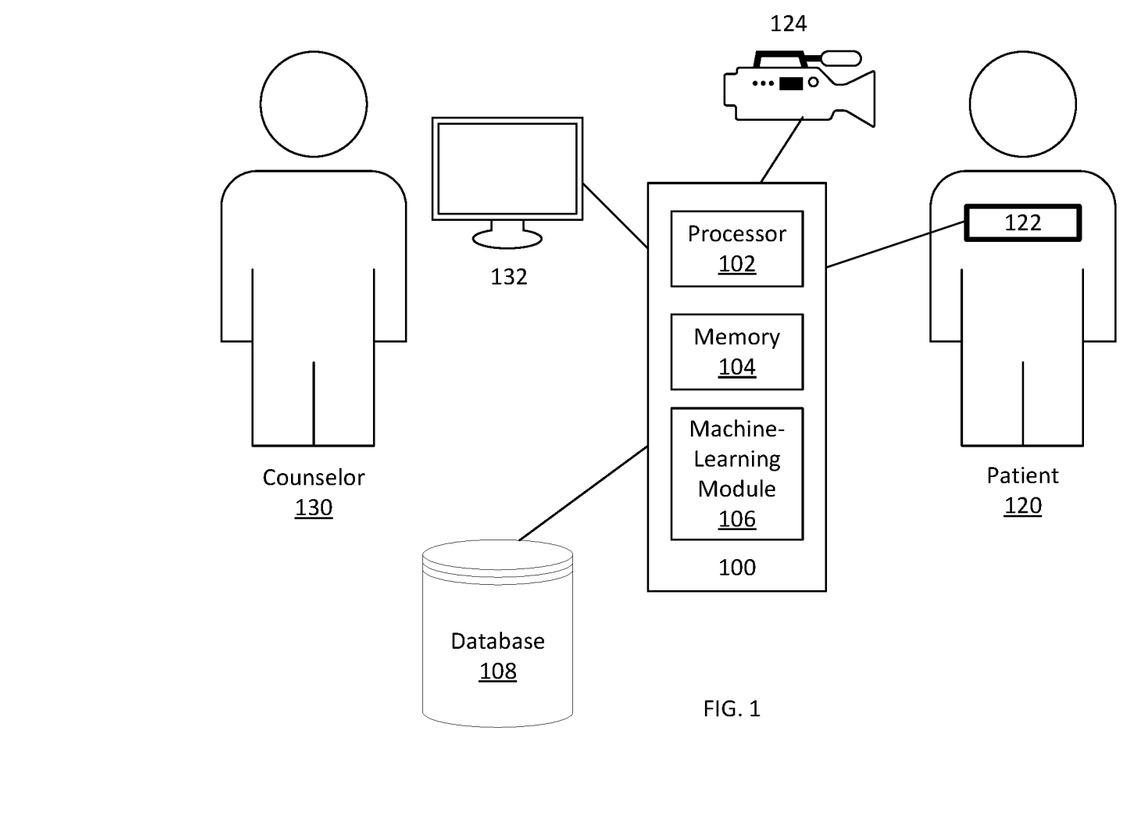
FIG. 1 is a schematic illustration of a system operable to analyzing counseling sessions, detecting aberrant reactions, and/or selecting improved treatment plans, according to an embodiment.

FIG. 1 is a schematic illustration of a system operable for analyzing counseling sessions, detecting aberrant reactions, and/or selecting improved treatment plans, according to an embodiment. A counseling session can involve a patient 120 and a counselor 130. The counseling session can be an in-person or tele-medicine session (e.g., facilitated by audio or video conferencing technology).

The system includes a compute device 100 that includes a processor 102, a memory 104, and a machine learning module 106. The processor 102 can be for example, a general purpose processor, a Field Programmable Gate Array (FPGA), an Application Specific Integrated Circuit (ASIC), a Digital Signal Processor (DSP), and/or the like. The processor 102 can be configured to retrieve data from and/or write data to memory, e.g., the memory 104, which can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. The compute device 100 can be one or more physical and/or logical devices. Similarly stated, the compute device 100 can be any number of networked processors and memories. The processors and memories can be physically identifiable devices such as servers, and/or virtual devices, such as cloud-implemented services.

The compute device 100 can be operable to receive data from and/or about the patient 120 and the counselor 130. In particular, the compute device 100 can receive biometric data captured by one or more biometric sensors 122 coupled to the patient. As discussed above, the biometric sensors 122 can include, for example and without limitation, heart rate sensors, blood pressure sensors, skin conductivity sensors, temperature sensors, and/or movement sensors. The compute device 100 can also receive biometric data from a video camera 124 trained on (i.e., detecting or capturing video of) the patient 120. The video camera 120 and/or the compute device 100 can be operable to analyze the video and determine, for example and without limitation, eye movement, body perspective or language, facial expressions, and so forth of the user. The compute device 100 can also receive demographic data for the patient 120, for example and without limitation, age, ethnicity, sex, veteran status, diagnostic information (such as treatment notes, mental illness diagnoses, distressing events, calming events, etc.) and so forth. The compute device 100 can further receive demographic data for the counselor 130. For example, the patient 120 and/or the counselor 130 can enter data into the compute device 100 via an input device (e.g., keyboard, personal computer, smart phone, etc.).

The compute device 100 can also be operably coupled to a database 108. The database 108 can store biometric information collected from other patients during other counseling sessions. The database 108 can also include patient identifiers, counselor identifiers, demographic information of patients, demographic information of counselors, indications of success and setbacks, and/or any other suitable information collected over previous counseling sessions. In some embodiments, the database 108 can include data from a large number of previous patients (e.g., 100, 1000, 10000, 100000, etc.) collected over a large number of counseling sessions (e.g., 500, 5000, 50000, 500000, etc.). The database 108 can include, for example, data similar to those example records shown in FIGS. 2-6. The compute device 110 and/or the database can be physically collocated with the counselor 130 and/or the patient 120 or can be remote devices, for example, physically present at one or more datacenters and/or implemented using a third-party commercial cloud services provider.

The compute device 100 can be operably coupled to an output device 132. The output device 132 can be, for example, a monitor configured to present visual information to the counselor 130 before, during, or after a counseling session. In this way, the compute device 100 can present demographic information collected from the patient 120, indications of whether the patient's 120 reactions are typical or aberrant, suggested modifications to the patient's treatment plan, warnings suggesting immediate intervention, and/or so forth to the counselor 130. In other embodiments, the output device 132 can present information to any suitable individual, such as the patient 120, a health care professional other than the counselor 130 overseeing the patient's treatment, a health insurance provider, and/or so forth.

The machine learning module 106 can be hardware and/or software (e.g., stored in memory 104 and/or executing on processor 102) configured to model patient reactions, predict effective treatments, and perform other functions described in further detail herein.

Figure 7:
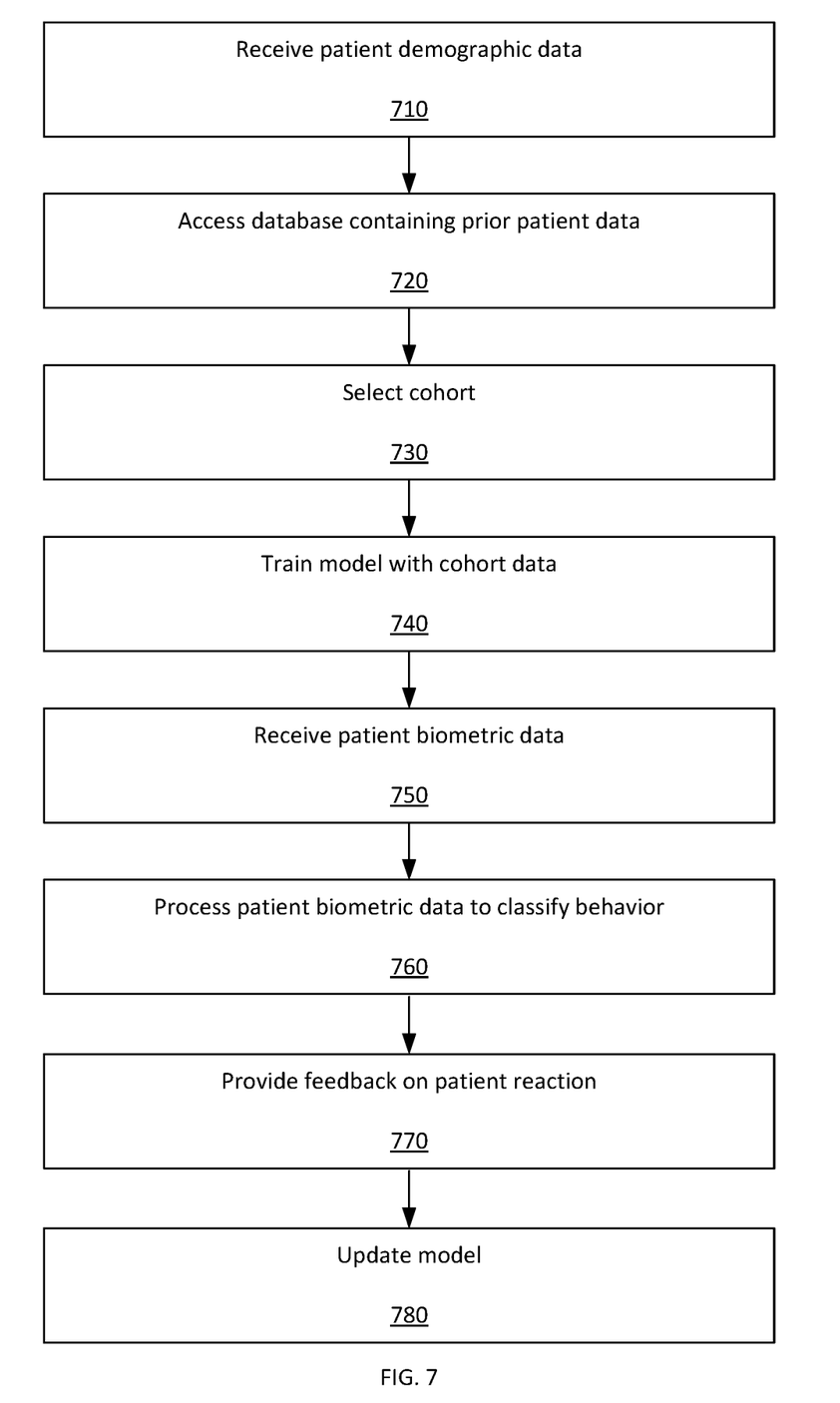
FIG. 7 is a flow chart of a method for training and applying a machine learning task, according to an embodiment.

FIG. 7 is a flow chart of a method for training and applying a model using machine learning tasks and/or techniques, according to an embodiment. At 710, a machine learning module (e.g., the machine learning module 106) can receive demographic information for a patient, (e.g., the patient 120). The demographic information for the patient can be sent from a counselor (e.g., the counselor 130), the patient, and/or retrieved from a database (e.g., the database 108). The demographic information for the patient can be similar to the information shown in FIG. 2.

Figure 2:
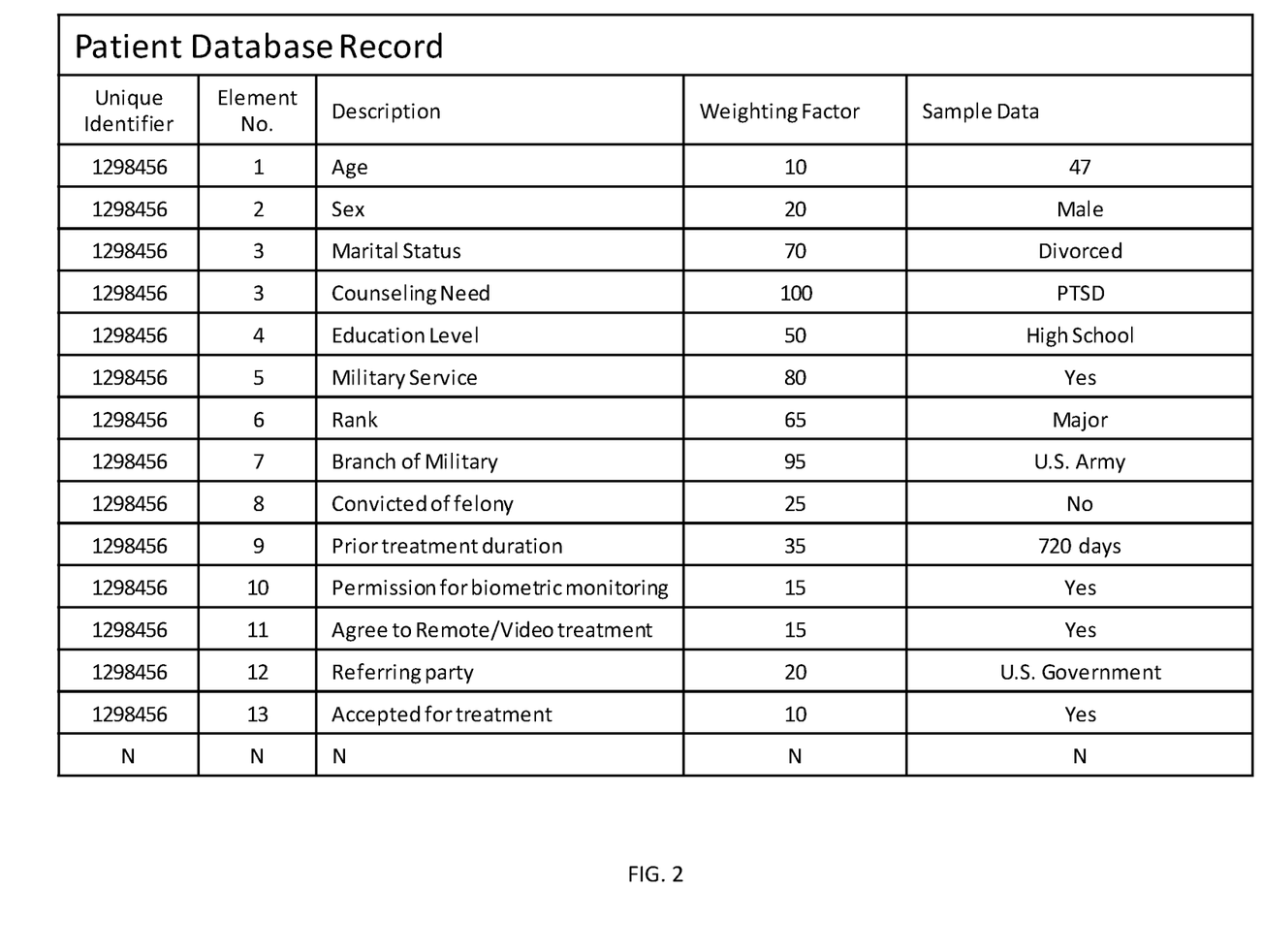
FIG. 2 is an example representing data records that are for a typical patient and that include various demographics related to the patient and the ability to add a weighting factor against each attribute for use in ranking relative importance for specific treatment programs.
Figure 3:
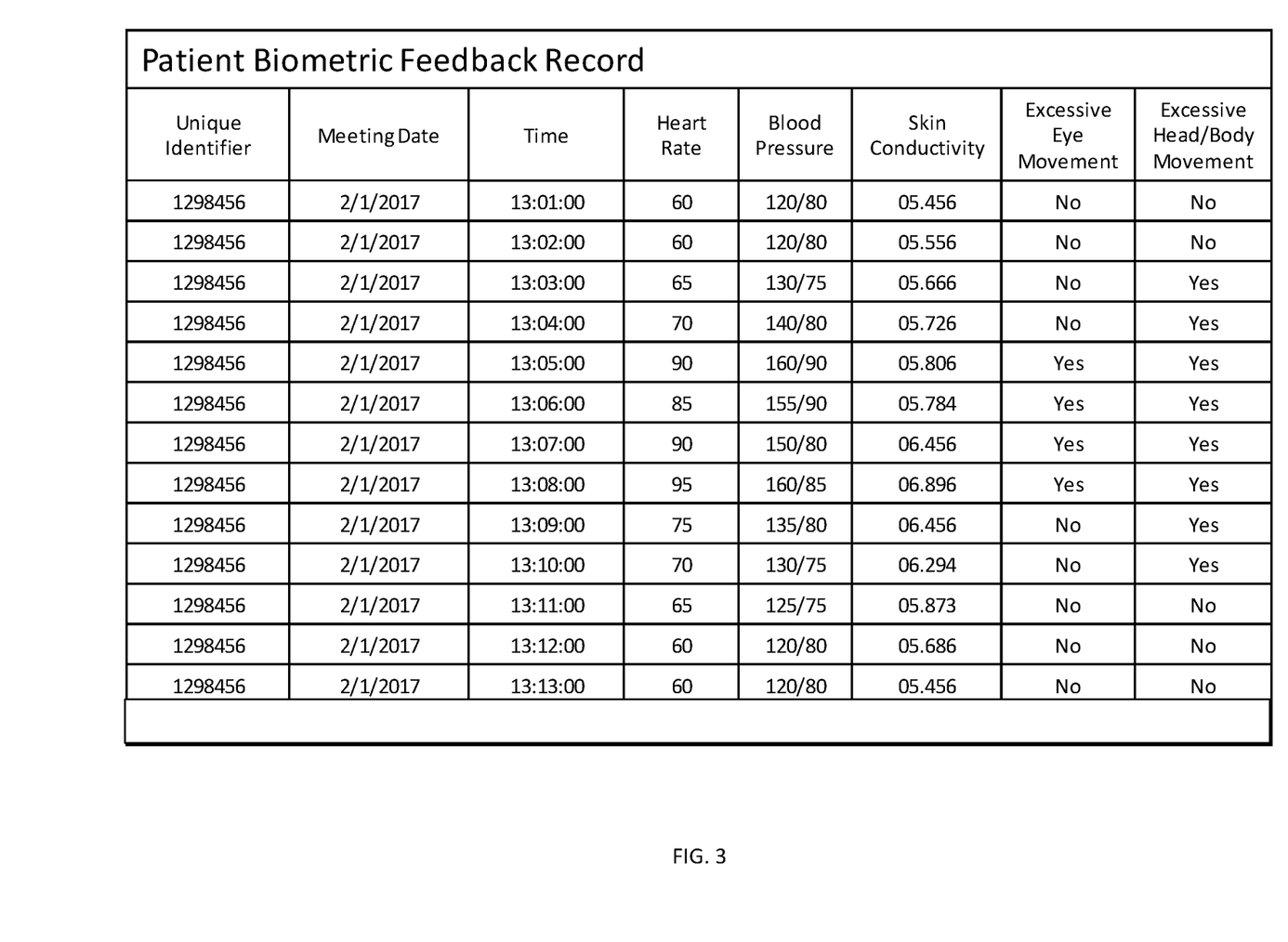
FIG. 3 is an example representing data records for each patient, including biometric data collected during each treatment session and time stamped. The frequency of collection will be determined by the biometric that is being collected. Some biometrics could be collected once per minute like blood pressure while others may involve constant, real-time monitoring like facial expressions.
Figure 4:
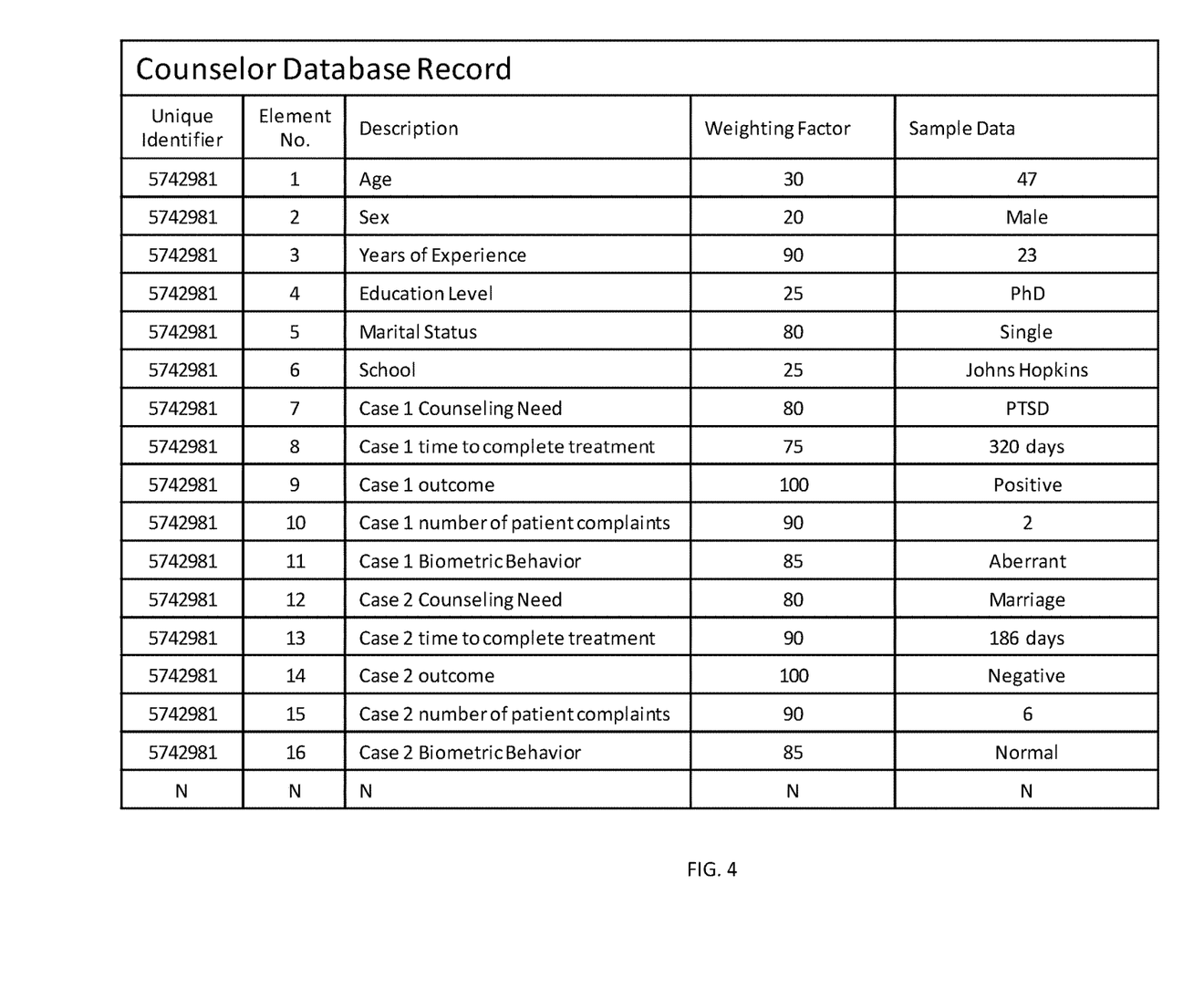
FIG. 4 is an example representing data records that are for a typical counselor and that include various demographics related to the counselor as well as a measure of their success in treating patients. The measure of success can include, for example, time to treat, biometric behavior feedback, and/or overall outcome.
Figure 5:
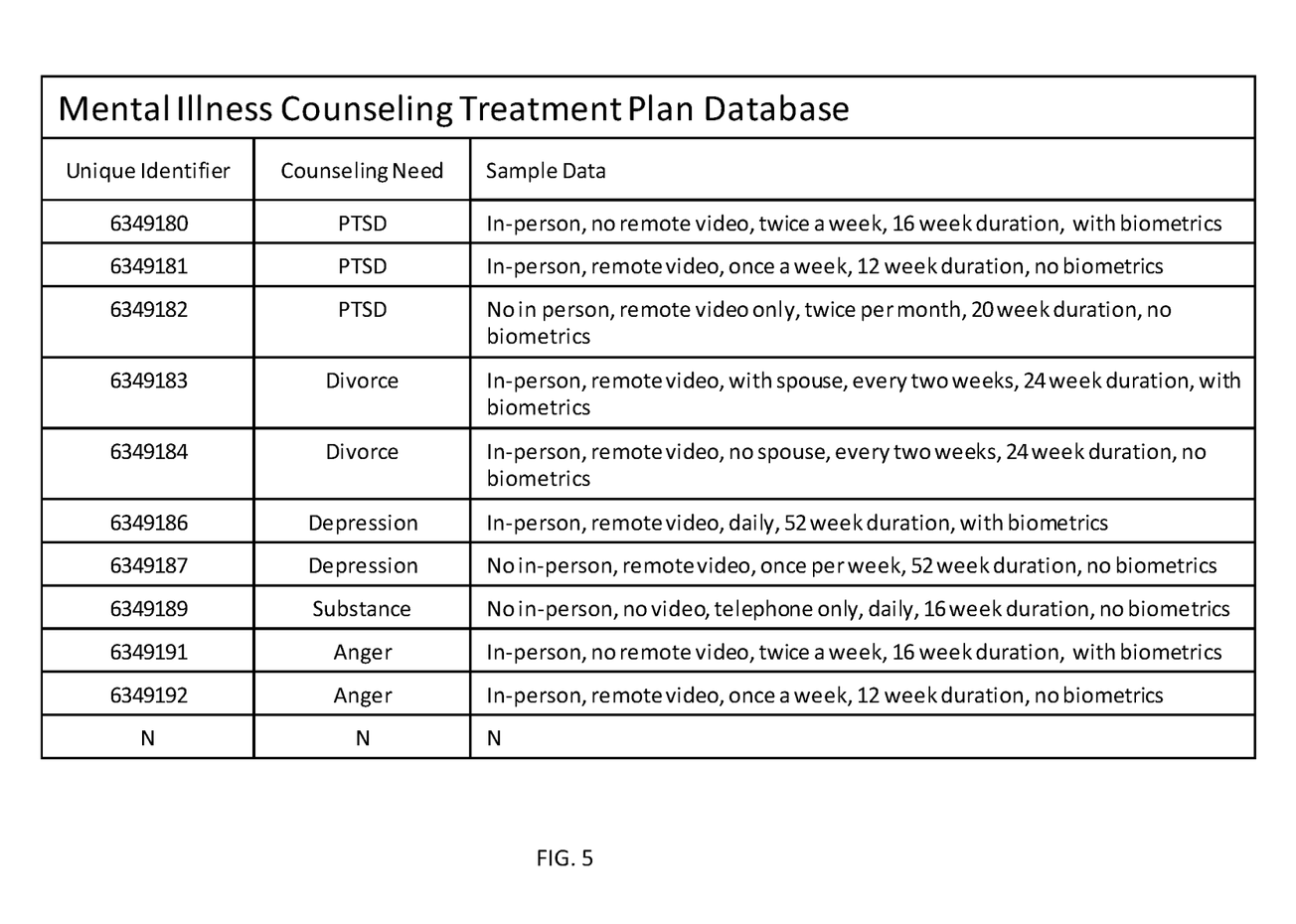
FIG. 5 is an example representing data records for the treatment of various mental illnesses. The treatment plans may be segmented into specific attributes and are unlimited in scope.
Figure 6:
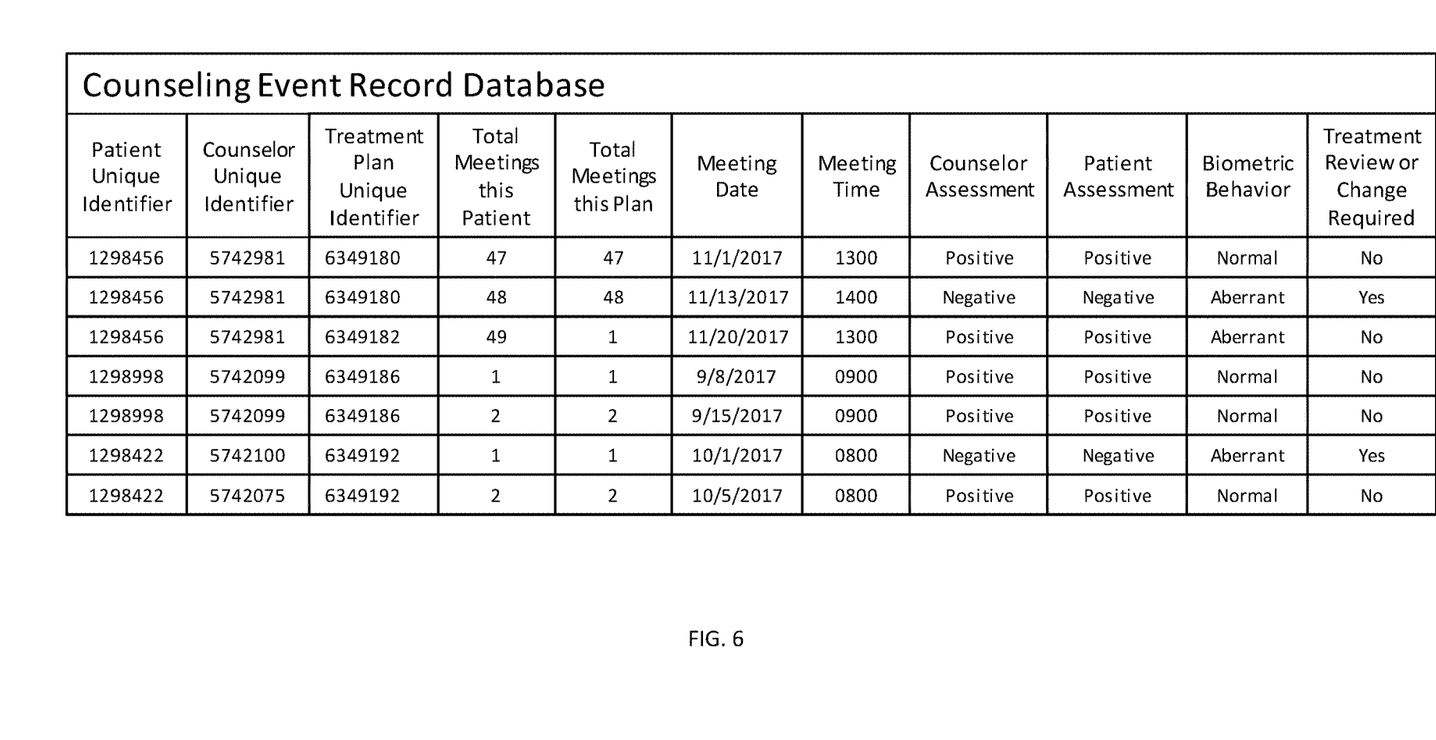
FIG. 6 is an example representing data records that track the progress within each treatment plan for a particular patient. Treatment plans can be changed for a patient multiple times while being treated for an illness and the number of sessions conducted are tracked for each plan. Both the counselor and the patient provide an assessment of each session. This is coupled with biometric behavior feedback, all of which are used to determine if a change in treatment plan is recommended.

At 720, the machine learning module can access records from the database (e.g., the database 108) containing biometric data for multiple patients (e.g., records similar to those shown in FIG. 3, but for multiple patients) and/or demographic data for multiple patients (e.g., records similar to those shown in FIG. 2, but for multiple patients). In some embodiments, the machine learning module can further access database records that include indications of treatment success and/or setbacks, such as records similar to those shown in FIG. 6. In some embodiments, the machine learning module can access biometric data and/or indications of treatment success and/or setbacks for the patient recorded during previous counseling sessions at 720.

At 730, the machine learning module can select a cohort that is demographically and/or biometrically similar to the patient. For example, the cohort can include patients of similar age (e.g., within 5 years), patients seeking counseling for a similar illness, patients with similar veteran status and/or service records, patients with similar treatment plans, and/or so forth. As another example, in some embodiments, the cohort can be selected based on a comparison of the patient's biometric parameters (e.g., as measured in a previous counseling session) to other patients' biometric parameters. For example, the cohort can include individuals having similar heart rate or other biometric responses to discussing traumatic incidents. In some embodiments, the cohort can only include the patient. Similarly stated, data for the "cohort" can be data associated with the patient that was collected during previous counseling sessions.

At 740, a machine learning task can define and/or train a model of patient behavior using data from the cohort. In some embodiments, the machine learning task can be supervised and train a model to identify treatment parameters and biometric data associated with successful treatment outcomes. In other embodiments, the machine learning task can be unsupervised (e.g., the model can be trained without indicating success conditions). The model produced by machine learning task can be based on the cohort and/or the illness for which treatment is sought, the demographic data of the individual and the counselor, the type and level of their response to follow-up feedback questioning concerning their treatment, and/or follow-up questioning. The model can therefore be specific to the patient and/or a particular counseling session (e.g., the current counseling session).

At 750, biometric data for the patient can be received. Biometric data can be received from one or more sensors coupled to or otherwise associated with the patient (e.g., a camera recording the patient and/or a microphone recording the patient). The biometric data can be received during a counseling session. At 760, the model trained at 740 can process the biometric data received at 750 and identify whether the patient is reacting typically or aberrantly. For example, if the biometric data received at 750 is consistent with positive treatment outcomes, consistent with biometric data previously identified as typical and/or healthy, and/or consistent with common biometric data, the model can identify the biometric data received at 750 as typical. Conversely, if the biometric data received at 750 is inconsistent with positive treatment outcomes, inconsistent with biometric data previously identified as typical and/or healthy, and/or inconsistent with common biometric data, the model can identify the biometric data received at 750 as aberrant.

In some embodiments, when biometric data is identified as corresponding to (or indicative of) an aberrant reaction, data associated with the aberrant reaction can be stored and studied to, for example, develop a new treatment plan, intervention, and/or modification of a treatment plan. If such a modified treatment plan is successful, for example, if a stimulus similar to that which caused the reaction identified as aberrant is applied according to a modified treatment plan and does not produce an aberrant reaction, the modified treatment plan can be stored into a database of available treatment plans and can be applied to the treatment of other patients.

Processing the data received at 750 using the model trained at 740 can identify or detect previously undetected, unrecognized, undetectable, and/or unrecognizable aberrant behavior. For example, one known method of detecting aberrant behavior relies on a counselor's subjective impression of the patient's affect. Applying the model at 760 is, in contrast, quantitative rather than qualitative, and does not rely on the counselor's training, experience with the patient, or other subjective analysis. The process of training a model at 740 and applying the model at 760 can quantitatively characterize various patents' reactions using a consistent process even though there may be no universal threshold for characterizing a reaction as aberrant. Moreover, applying a model defined using a machine learning task goes beyond simply matching observed biometric data to a list of aberrant biometric conditions. Similarly stated, processing the data received at 750 using a model defined or trained using machine learning tasks does not involve simply comparing biometric data to predefined thresholds. Similarly stated, any thresholds or scores for determining whether a reaction is aberrant are not pre-defined prior to the training a patient-specific model at 740. Instead, the use of a model defined using a machine learning task allows the compute device to produce biometrically informed evaluations of a patient's reaction to therapy and provide additional insights into patient reactions as compared to simple comparisons of biometric data to thresholds. In this way, the machine learning task can identify aberrant reactions that do not conform to a predefined type of aberrant reaction. Similarly stated the identification of aberrant reactions can be emergent. Furthermore, by modeling multiple biometric parameters in combination, aberrant behaviors that would appear typical based on one or any biometric parameter viewed in isolation can be identified. For example, on their own, a mildly elevated heart rate, mildly elevated skin conductivity, and mildly evasive eye movements may be typical. In combination and for some cohorts, however, the combination may signal an aberrant reaction.

At 770, an indication of the typicality and/or aberrancy of the biometric data can be sent to, for example, the counselor (e.g., via the output device 132). In addition or alternatively, the model and/or machine-learning task can suggest treatment modifications at 770. Treatment modifications can include, for example and without limitation, changing the topic of conversation, practicing coping techniques, suggesting more frequent and/or additional counseling sessions, focusing on the topic that triggered the aberrant reaction (e.g., as an element of prolonged exposure therapy), suggesting medication, and so forth. In some instances, the treatment modification suggested at 770 can be the selection of another counselor, for example, a counselor of a different sex, age, experience, etc. Similarly stated, in some embodiments, the machine learning task can be configured to recognize that the patient-counselor pairing could be improved. When the machine learning task suggests the selection of another counselor, the patient can be counseled by a new counselor in a subsequent session.

In some embodiments, processing biometric data at 760 can identify a mental health crisis in real-time. For example, the model can be operable to identify when a patient undergoing treatment for post-traumatic stress disorder is experiencing flashbacks or panic attacks. The model can similarly be operable to identify a variety of severe reactions that have the potential to negatively affect the treatment. The machine learning task can further be operable to identify an immediate intervention suitable to minimize or reverse the crisis. For example, the machine learning task can compare biometric data associated with the patient undergoing the mental health crisis to data collected from previous patients who may have experienced a similar reaction. The machine learning task can further associate interventions that were previously successful in reducing or reversing the crisis. At 770, a warning alerting the counselor to the crisis and/or suggesting an intervention or treatment to treat the crisis can be sent, for example, during the treatment or after the treatment (e.g., if the crisis is acute). In some embodiments, therefore, the system can provide immediate alerts or warnings to the counselor to minimize the effects of a crisis in real time.

Figure 10:
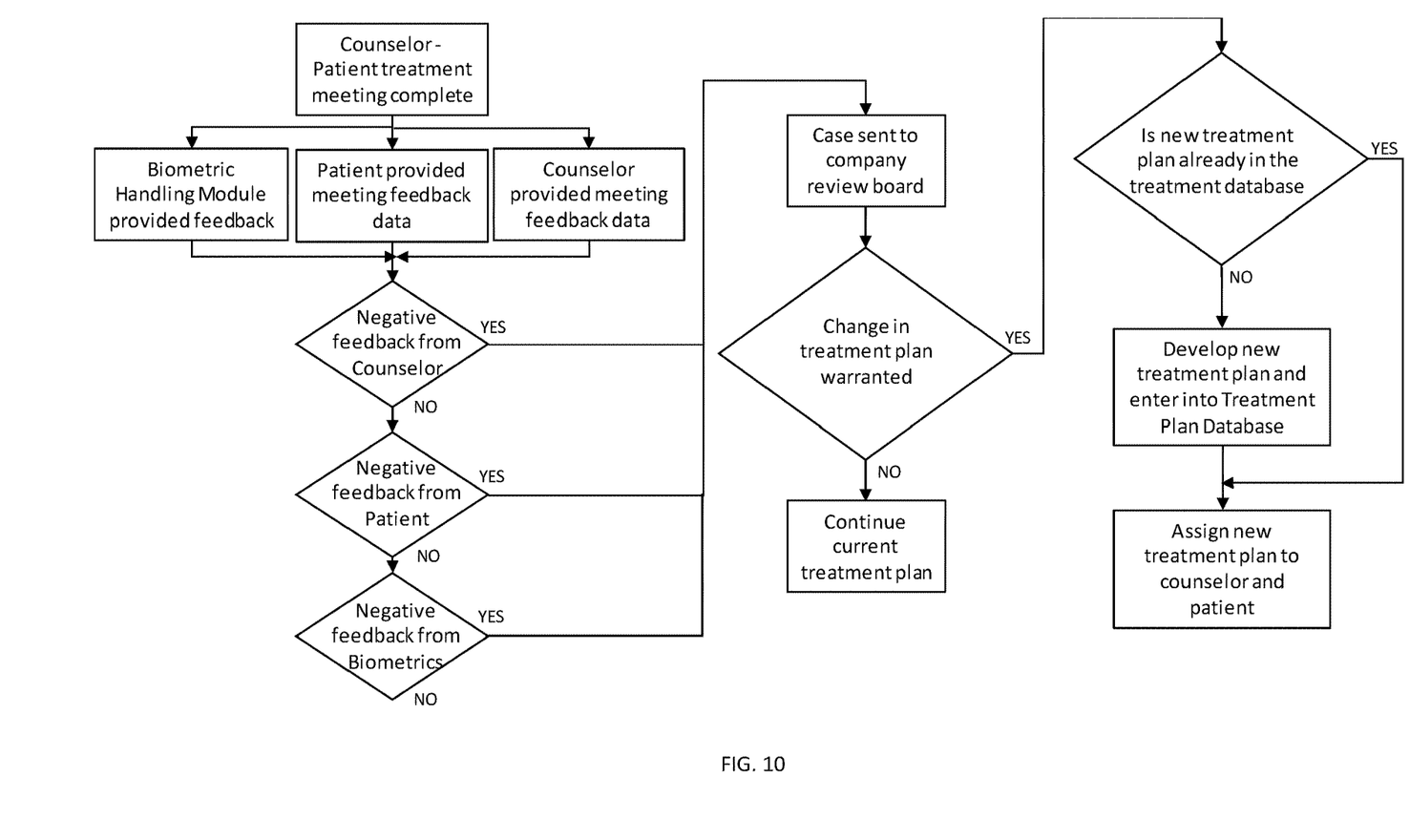
FIG. 10 is a flow chart of a method that includes changing treatment plans and developing new treatment plans, according to an embodiment.

In some embodiments, providing feedback on patient reactions can be long-term feedback. FIG. 10 is a flow chart of a method that, according to an embodiment, includes changing treatment plans, when warranted, and developing new treatment plans, when appropriate. FIG. 10 illustrates one method for providing feedback on a patient's reaction, at 770 (of FIG. 7). In particular, feedback from the counselor, the patient, and/or analysis of collected biometric data can be processed by a machine learning task and/or a review board (e.g., a panel of experts set up by a company offering counseling services) to determine whether a change in treatment plan is warranted. If a change in treatment plan is warranted (e.g., the feedback from patient, counselor, and/or biometric data indicates that the current treatment plan is unsuccessful or could be improved), a new treatment plan can be selected. In some embodiments, a database can store multiple treatment plans and/or treatment modifications. The machine learning task can process feedback from the patient, counselor, and/or biometric data and identify and/or recommend a treatment plan. In an instance where a suitable treatment plan or modification is not identified, a new treatment plan can be created (or defined) by the review board and/or the machine learning task. For example, the machine learning task can extrapolate existing treatment plans to new cohorts or patients. The new treatment plan can be assigned at 770.

At 780, the model can be updated (e.g., retrained) with the biometric data collected at 750 and/or indications of success associated with the counseling session for which biometric data was collected at 750. In this way, biometric data previously identified as aberrant could, in the future, be identified as typical, for example, as additional data is collected that reveals that the biometric data previously identified as aberrant is more common than previously observed, as additional data is collected that reveals that the biometric data previously identified as aberrant is associated with positive treatment outcomes, and/or so forth. For example, training a model at 740 and/or updating a model at 780 can include analyzing biometric data associated with a cohort. If biometric data associated with a behavior that was considered typical is observed occurring less often than was previously expected (e.g., as predicted by the model) and/or if additional data reveals that behaviors previously identified as typical are negatively correlated with successful treatments, such a behavior can be reclassified as aberrant. Conversely, if biometric data associated with a behavior that was previously considered aberrant occurs more frequently than was previously expected (e.g., as predicted by the model) and/or if additional data reveals that behaviors previously identified as aberrant are positively correlated with successful treatments, such a behavior can be reclassified as typical.

Thus, the machine learning task is adaptive and models defined by the machine learning task can change as additional data associated with a particular patient, the cohort, the disease, and/or any other suitable data is received. With the addition of every new patient into the system, their treatment plan, demographic information, and treatment duration, collected biometrics, and treatment outcome can be added to the database, which the machine learning task can use to train (or retrain) models. In this manner, models produced by the machine learning task become more accurate with each additional patient and associated element of data that is added.

With the addition of every new counselor into the system, their demographic information, and treatment duration, and treatment outcome can be added to the database and can be used by the machine leaning task to train (or retrain) models of patient behavior. In this manner, models produced by the machine learning task become more accurate with each additional counselor and associated element of data that is added.

The machine learning task can further provide predictions and/or recommendations relating to new patients, existing patients, counselors, and business operation. For patients, these could be but are not limited to the continued treatment under a current plan, treatment moving forward with a new or modified plan, or possibly to request immediate intervention with the patient by either a counselor or law enforcement to ensure the patient's safety.

A predictive model of patient behavior is operable to classify monitored biometric data as either typical or aberrant for a particular patient, cohort of patient, and/or condition. Whether a particular set of biometric data received during a counseling session is classified as typical or aberrant is not pre-determined before the model is trained, before a particular patient begins treatment, and/or before a particular counseling session. Similarly stated, according to some embodiments, the machine learning task does not apply a fixed formula or thresholds to biometric data to determine whether a behavior is typical or aberrant. When a particular biometric behavior is seen with a high degree of frequency, it can be assigned a "typical" classification for that cohort. When a recorded biometric has never been seen before for that patient cohort, it can be classified as aberrant and triaged for possible action as part of the treatment plan. This action may occur as a part of immediate treatment changes or for out-of-treatment actions with family, medical professional or legal authorities. It would be a typical action for the learning system to move some behaviors originally classified as aberrant to typical if their frequency of occurrence warrants.

The predictive machine learning task could be run (e.g., training and/or retraining a model) at specific times, at specific intervals, or be triggered by any number of events that change or add data concerning anything about a patient or the counselor.

Many types of machine learning tasks can be used in this application, however, some are more suited to generate models for predicting user behavior than other machine learning tasks. The solution may entail one or more models to provide the level of predictive accuracy and prescriptive solutions that are desired. For those biometric factors that are known non-standard behaviors, a supervised model could be used where it could be easily trained to recognize those behaviors. A more difficult problem to solve is to find those hidden behaviors that are unknown today and would involve more of an unsupervised model to explore the data looking for relevant clusters. The clustering may be accomplished through one or several algorithms. For instance, a K-means clustering analysis would fit well for discerning relationships between a specific patient and all patient groups. This would lead to identifying effective treatment relationships that would not otherwise be seen. Other options that would be tailored to meet specific treatment/ patient classification and grouping goals would include Hierarchical, Gaussian mixture, Neural Nets, and Hidden Markov models.

Figure 8:
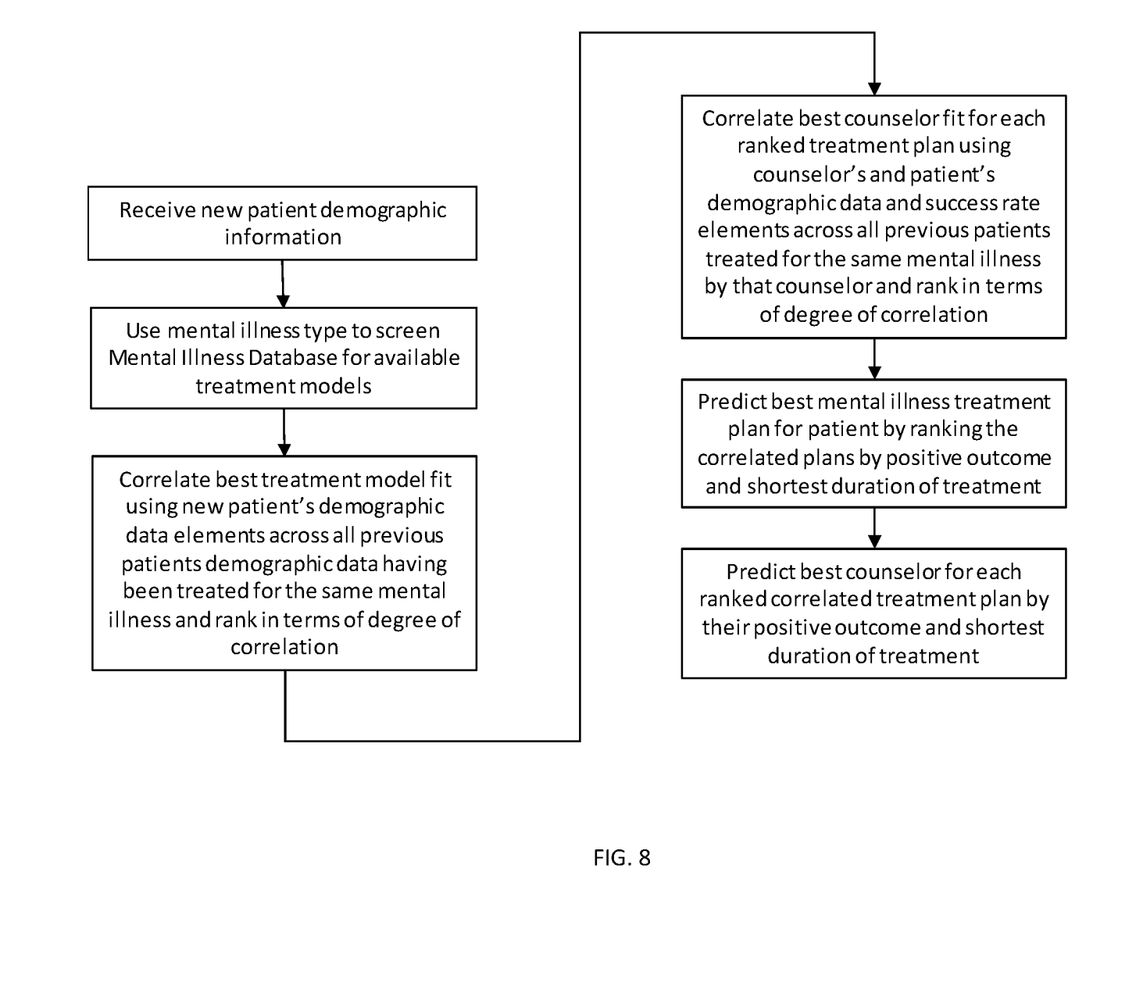
FIG. 8 is a flow chart of a method that includes identifying mental illness treatment plans and counselors for a patient, according to an embodiment.
Figure 9:
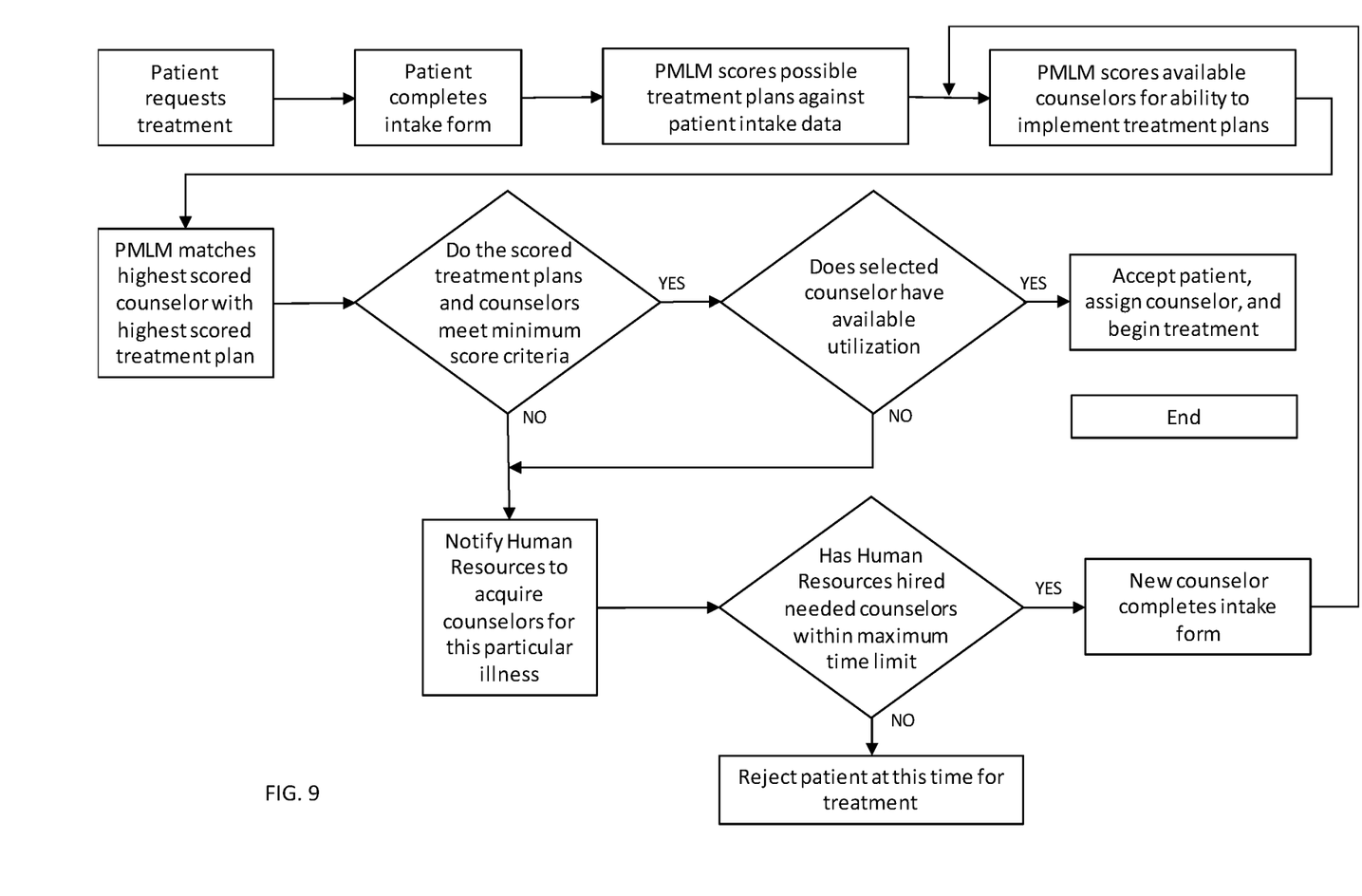
FIG. 9 illustrates flow chart of a method that includes matching counselors with patients based on Patient Machine Learning Module (PMLM), according to an embodiment.

Some embodiments described herein involve estimating what will happen next with a particular patient based upon multiple data factors including collected biometrics. In some embodiments, prescriptive analytics can further suggest actions to take in the treatment of patients to achieve improved outcomes. Similarly stated, although embodiments described herein generally relate to descriptive use of models (e.g., is a patient's reaction typical or aberrant), such models can also be used to prescribe therapeutic techniques that minimize aberrant reactions or seek to induce aberrant reactions where therapeutically beneficial. A personalized plan for each patient can be defined based upon their interactions with various treatment options and counselors. In this way, the data will help to drive the treatment instead of having the treatment rely only on pre-existing symptomatic belief sets or known treatment options. FIG. 8, for example, is a flow chart of a method that includes identifying mental illness treatment plans and counselors for a patient. FIG. 9 illustrates flow chart of a method that, in an embodiment, includes matching counselors with patients based on Patient Machine Learning Module (PMLM), which can be structurally and/or functionally similar to the machine learning module 106 described above with reference to FIG. 1, and sending signals to suitable human resources systems or individuals to acquire additional counselors.

A known challenge facing psychological practices is evaluating counselors and matching counselors to patients. An aspect of some embodiments can aid such practices by, for example, using an adaptive and/or predictive model to analyze the currently employed counselors for their top effectiveness in treating patients with specific mental illnesses. Such a model may reveal for example, that some counselors are particularly effective at treating certain mental illnesses and/or cohorts and less effective at treating other mental illnesses and/or cohorts. Thus, predictive models described herein can be used to steer patients to counselors who are particularly effective at treating that type of patient. Likewise, the embodiments described herein can be used to identify trends in the types of patients that are being served and to then predict what types and quantities of specific future counselors will be needed to serve that predicted population if the trends continue. Such models may also be used to provide feedback to counselors, for example, as part of a review of the counselor's overall effectiveness and/or effectiveness dealing with certain illnesses and/or cohorts. Additionally, such models may be able to more efficiently utilize counselors, for example, by "right-sizing" a counseling practice.

Machine learning tasks described herein can be used to learn from published medical studies and other repositories of treatment efficacy information to offer suggestions for treatment that meet the criteria set forth in the studies with those of actual patients. These recommendations, once approved by a company internal review board, could be given to both the counselor working with the patient as well as the management team of the business to approve for use.

Approved treatment plans would then be incorporated into the overall machine model for continued future use.

While various embodiments have been described herein, it should be understood that they have been presented by way of example only, and not limitation. For example, some embodiments describe a machine learning task or a model being used to predict patient reactions. It should be understood, however, that any number of machine learning tasks can be used to define and/or train any number of models of patient behavior. For example, multiple models of a single patient's behavior can be defined and/or trained. In some such instances, models that most accurately predict the patient's actual responses can be more heavily weighted and/or selected for providing counseling session feedback, interventions, and/or treatment plan modifications.

Furthermore, although various embodiments have been described as having particular features and/or combinations of components, other embodiments are possible having a combination of any features and/or components from any of embodiments where appropriate as well as additional features and/or components.

Where methods described herein indicate certain events occurring in certain order, the ordering of certain events may be modified. Additionally, certain of the events may be performed repeatedly, concurrently in a parallel process when possible, as well as performed sequentially as described above. Furthermore, certain embodiments may omit one or more described events. Where methods are described, it should be understood that such methods can be computer-implemented methods. Similarly stated, a non-transitory processor readable medium can store code representing instructions configured to cause a processor to cause the described method to occur or be carried out.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A system, comprising:
   at least one of (1) a video camera configured to capture video data or (2) an audio recorder configured to capture audio data, of a patient during a counseling session; and
   at least one compute device operably coupled to the at least one of the video camera or the audio recorder, the at least one compute device configured to:
      extract biometric data from at least one of the video data or the audio data, the biometric data including at least one of eye movement, body perspective, body language, facial expression, word selection, sentence structure, pauses in speech, length of a response to a question, or timeliness of the response to the question;
      identify the patient as being a member of a cohort based on at least one of (i) the biometric data or (ii) demographic information for the patient;
      perform a machine learning task on the biometric data to identify an aberrant reaction of the patient relative to at least one of a typical reaction of the patient or a reaction typical to the cohort to which the patient belongs, the machine learning task configured to quantitatively identify the aberrant reaction of the patient without comparing the plurality of biometric parameters to predefined thresholds;
      define a modified treatment plan based on the aberrant reaction being identified; and
      update the machine learning task with information associated with the aberrant reaction such that repeated occurrences of the aberrant reaction will cause the machine learning task to relabel the aberrant reaction as a typical reaction.

2. The system of claim 1, wherein the biometric data includes at least two of the eye movement, the body perspective, the body language, the facial expression, the word selection, sentence structure, the pauses in speech, the length of the response to the question, or timeliness of the response to the question.

3. The system of claim 1, wherein the aberrant reaction does not correspond to a predefined type of aberrant reaction.

4. The system of claim 1, wherein the biometric data on which the machine learning task is performed and based on which the aberrant reaction is identified does not correspond to a pattern of biometric parameters previously identified as corresponding to an aberrant reaction.

5. The system of claim 1, wherein the patient and the at least one of the video camera or the audio recorder are at a first location and at least one of the at least one compute device or a counselor administering the counseling session are at a second location remote from the first location.

6. The system of claim 1, wherein:
   the at least one compute device is operably coupled to a database containing biometric parameters for a plurality of previous patients and an indication of treatment outcome for each previous patient from the plurality of previous patients;
   the cohort includes a subset of the plurality of previous patients; and
   the at least one compute device is configured to train the machine learning task using the biometric parameters for the subset of the plurality of previous patients.

7. The system of claim 1, further comprising an output device is configured to warn a counselor administering the counseling session of the aberrant reaction.

8. At least one compute device operably coupled to at least one of (1) a video camera configured to capture video data or (2) an audio recorder configured to capture audio data, of a patient during a counseling session administered by a first counselor, the at least one compute device configured to:

extract biometric data from at least one of the video data or the audio data, the biometric data including at least one of eye movement, body perspective, body language, facial expression, word selection, sentence structure, pauses in speech, length of a response to a question, or timeliness of the response to the question;
identify the patient as being a member of a cohort based on at least one of (i) the biometric data or (ii) demographic information for the patient;
perform a machine learning task on the biometric data to identify an aberrant reaction of the patient relative to at least one of a typical reaction of the patient or a reaction typical to the cohort to which the patient belongs, the machine learning task configured to quantitatively identify the aberrant reaction of the patient without comparing the plurality of biometric parameters to predefined thresholds; and
define a modified treatment plan based on the aberrant reaction being identified, the modified treatment plan including an indication that the patient should be treated by a second counselor different from the first counselor.

9. The at least one compute device of claim 8, wherein the biometric data includes at least two of the eye movement, the body perspective, the body language, the facial expression, the word selection, the sentence structure, the pauses in speech, the length of the response to the question, or the timeliness of the response to the question.

10. The at least one compute device of claim 8, wherein:
the counseling session is associated with a treatment plan for post-traumatic stress disorder;
the aberrant reaction is associated with anxiety related to a trauma; and
the modified treatment plan includes refocusing the counseling session away from the trauma to reduce the anxiety.

11. The at least one compute device of claim 8, wherein:
the counseling session is associated with a treatment plan for post-traumatic stress disorder;
the aberrant reaction is associated with anxiety related to a trauma; and
the modified treatment plan includes focusing on the trauma in connection with prolonged exposure therapy.

12. The at least one compute device of claim 8, wherein:
the at least one compute device is configured to identify the aberrant reaction by identifying a mental health crisis in real-time; and
the at least one compute device is configured to define the modified treatment plan by identifying a therapeutic intervention to reduce an impact of the mental health crisis.

13. The at least one compute device of claim 8, wherein:
the at least one compute device is operably coupled to a database containing biometric parameters for a plurality of previous patients and an indication of treatment outcome for each previous patient from the plurality of previous patients;
the cohort includes a subset of the plurality of previous patients; and
the at least one compute device is configured to train the machine learning task using the biometric parameters for the subset of the plurality of previous patients.

14. At least one compute device operably coupled to at least one of (1) a video camera configured to capture video data or (2) an audio recorder configured to capture audio data, of a patient during a counseling session administered by a first counselor, the at least one compute device configured to:
extract biometric data for the patient from at least one of the video data or the audio data, the biometric data including at least one of eye movement, body perspective, body language, facial expression, word selection, sentence structure, pauses in speech, length of a response to a question, or timeliness of the response to the question;
identify the patient as being a member of a cohort based on at least one of (i) the biometric data for the patient or (ii) demographic information for the patient;
train a supervised machine learning model with biometric data for the cohort, after training the supervised machine learning model being configured to perform a machine learning task;
apply the machine learning task to the biometric data for the patient to identify an aberrant reaction; and
define a modified treatment plan based on the aberrant reaction being identified.

15. The at least one compute device of claim 14, further comprising an output device communicatively coupled to the at least one compute device and configured to produce a warning signal that alerts a counselor to employ the modified treatment plan.

16. The at least one compute device of claim 14, wherein the at least one compute device is further configured to update the machine learning task with information associated with the aberrant reaction such that repeated occurrences of the aberrant reaction will cause the machine learning task to relabel the aberrant reaction as a typical reaction.

17. A system, comprising:
at least one of (1) a video camera configured to capture video data or (2) an audio recorder configured to capture audio data, of a patient during a counseling session;
at least one compute device operably coupled to the at least one of the video camera or the audio recorder, the at least one compute device configured to:
extract biometric data for the patient from at least one of the video data or the audio data, the biometric data including at least one of eye movement, body perspective, body language, facial expression, word selection, sentence structure, pauses in speech, length of a response to a question, or timeliness of the response to the question;
identify the patient as being a member of a cohort based on at least one of (i) the biometric data for the patient or (ii) demographic information for the patient; and
perform an machine learning task on the biometric data for the patient to identify an aberrant reaction of the patient, the machine learning task being associated with an unsupervised machine learning model trained on biometric data for the cohort without associating biometric data for the cohort with a success metric.

18. The system of claim 17, wherein the at least one compute device is further configured to:
define a modified treatment plan based on the aberrant reaction being identified; and
update the machine learning task with information associated with the aberrant reaction such that repeated occurrences of the aberrant reaction will cause the machine learning task to relabel the aberrant reaction as a typical reaction.

19. The system of claim 17, wherein:
- the at least one compute device is operably coupled to a database containing biometric parameters for a plurality of previous patients and an indication of treatment outcome for each previous patient from the plurality of previous patients;
- the cohort includes a subset of the plurality of previous patients; and
- the at least one compute device is configured to train the unsupervised machine learning model using the biometric parameters for the subset of the plurality of previous patients.

20. The system of claim 17, wherein the biometric data includes at least two of the eye movement, the body perspective, the body language, the facial expression, the word selection, the sentence structure, the pauses in speech, the length of the response to the question, or the timeliness of the response to the question.

* * * * *